United States Patent [19]
Bantick et al.

[11] Patent Number: 5,935,956
[45] Date of Patent: Aug. 10, 1999

[54] PYRIDAZINE COMPOUNDS

[75] Inventors: John Bantick, Burton-on-the-Wolds; Simon Hirst, West Bridgford; Matthew Perry, Loughborough, all of United Kingdom

[73] Assignee: Astra Pharmaceuticals Ltd., Herts, United Kingdom

[21] Appl. No.: 08/913,060

[22] PCT Filed: May 20, 1997

[86] PCT No.: PCT/SE97/00818

§ 371 Date: Sep. 5, 1997

§ 102(e) Date: Sep. 5, 1997

[87] PCT Pub. No.: WO97/45428

PCT Pub. Date: Dec. 4, 1997

[30] Foreign Application Priority Data

May 24, 1996 [GB] United Kingdom .................... 9610893

[51] Int. Cl.$^6$ .......................... C07D 471/04; A61K 31/50
[52] U.S. Cl. .......................... 514/247; 514/252; 544/234; 544/244; 544/250

[58] Field of Search ..................................... 544/244, 250; 514/247, 252

[56] References Cited

U.S. PATENT DOCUMENTS

| | | | |
|---|---|---|---|
| 5,340,808 | 8/1994 | Jean et al. | 514/248 |
| 5,597,918 | 1/1997 | Nakao et al. | 544/234 |

FOREIGN PATENT DOCUMENTS

| | | | |
|---|---|---|---|
| 351435 | 5/1989 | European Pat. Off. | C07D 237/36 |

*Primary Examiner*—Jose' G. Dees
*Assistant Examiner*—Sabiha N. Qazi
*Attorney, Agent, or Firm*—Nixon & Vanderhye

[57] ABSTRACT

The invention relates to fused pyridazine compounds, in particular pyrido [h]cinnoline, pyrido[h]cinnolinone, pyridocyclopenta[1,2-c]pyridazine, pyridocyclopenta[1,2-c]pyridazinone, pyridocyclohepta[1,2-c]pyridazine and pyridocyclohepta[1,2-c]pyridazinone derivatives, their use as medicaments and pharmaceutical compositions comprising them.

10 Claims, No Drawings

PYRIDAZINE COMPOUNDS

This application has been filed under 35 USC 371 as a national stage application of PCT/USE 97/00818, filed May 20, 1997.

The present invention relates to fused pyridazine compounds, in particular pyrido[h]cinnoline, pyrido[h]cinnolinone, pyridocyclopenta[1,2-c]pyridazine, pyridocyclopenta[1,2-c]pyridazinone, pyridocyclohepta[1,2-c]pyridazine and pyridocyclohepta[1,2-c]pyridazinone derivatives, their use as medicaments and pharmaceutical compositions comprising them.

EPA 0 351 435 discloses a series of fused pyridazine compounds which are said to be useful for the treatment of various diseases associated with immune function deficiency. A series of structurally distinct compounds have now been discovered and surprisingly found to possess anti-allergic and anti-inflammatory activity.

In a first aspect the invention therefore provides a compound of formula I:

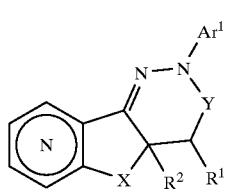

(I)

wherein

X is $(CH_2)_n$ or CH=CH;

n is 1,2 or 3;

Y is $CH_2$ or C=O;

$R^1$ is hydrogen or together with $R^2$ is a bond;

$R^2$ is hydrogen, $C_{1-6}$ alkyl or together with $R^1$ is a bond; and $Ar^1$ represents thiazolyl, phenyl, pyridyl, pyrimidinyl, 2-benzothiazolyl, 2- or 3-quinolyl or 2-quinoxalinyl (all of which are optionally substituted by one or more substituents selected from halo, nitro, cyano, phenyl, phenylsulfonyl, $C_{1-6}$ alkyl, $C_{1-6}$ alkoxy, $C_{1-6}$ alkylthio, $C_{1-6}$ alkylsulfinyl, COOH, COO($C_{1-6}$alkyl), $CONH_2$, $C_{1-6}$ alkyl substituted by phenyl, or phenyl, in which any alkyl, alkoxy, alkylthio and alkylsulfinyl groups may optionally be substituted by one or more fluorine atoms;

provided that when Y is $CH_2$, $R^1$ and $R^2$ do not together represent a bond; and pharmaceutically acceptable derivatives thereof.

Alkyl groups, whether alone or as part of another group, can be linear or branched.

Pharmaceutically acceptable derivatives include solvates, N-oxides and salts. For example the compounds of the formula (I) can form acid addition salts with acids, such as conventional pharmaceutically acceptable acids, for example maleic, hydrochloric, hydrobromic, phosphoric, acetic, fumaric, salicylic, citric, lactic, mandelic, tartaric and methanesulphonic acids.

Suitably X is $(CH_2)_n$ or CH=CH, preferably X is $(CH_2)_n$ preferably where n is 2.

Suitably $R^1$ is hydrogen or together with $R^2$ is a bond. Preferably $R^1$ is hydrogen.

Suitably $R^2$ is hydrogen, $C_{1-6}$ alkyl or together with $R^1$ is a bond. Preferably $R^2$ is hydrogen.

Suitably $Ar^1$ represents thiazolyl, phenyl, pyridyl, pyrimidinyl, 2-benzothiazolyl, 2- or 3-quinolyl or 2-quinoxalinyl (all of which are optionally substituted by one or more substituents selected from halo, nitro, cyano, phenyl, phenylsulfonyl, $C_{1-6}$ alkyl, $C_{1-6}$ alkoxy, $C_{1-6}$ alkylthio, $C_{1-6}$ alkylsulfinyl, COOH, COO($C_{1-6}$ alkyl), $CONH_2$, $C_{1-6}$alkyl substituted by phenyl, or phenyl, in which any alkyl, alkoxy, alkylthio and alkylsulfinyl groups may optionally be substituted by one or more fluorine atoms. Preferably $Ar^1$ is phenyl optionally substituted by one or more substituents selected from $C_{1-6}$alkyl, halogen, nitro, cyano or $CF_3$. Most preferably $Ar^1$ is phenyl optionally substituted by one or two substituents selected from halogen, methyl or trifluoromethyl, particularly trifluoromethyl.

Suitably Y is $CH_2$ or C=O, preferably Y is C=O.

The nitrogen atom in the left ring of the compounds of formula (I) can be in any position. Preferably, when X forms part of a 6-membered ring, the nitrogen atom is in the 7- or 9-position.

The compounds of formula I may exhibit tautomerism. All tautomeric forms and mixtures thereof are included within the scope of the invention. The compounds of formula I may also contain one or more asymmetric carbon atoms and may therefore exhibit optical and/or diastereoisomerism. All diastereoisomers may be separated using conventional techniques, eg. chromatography or fractional crystallisation. The various optical isomers may be isolated by separation of a racemic or other mixture of the compounds using conventional, eg. fractional crystallisation or HPLC, techniques. Alternatively the desired optical isomers may be made by reaction of the appropriate optically active starting materials under conditions which will not cause racemisation, or by derivatisation, for example with a homochiral acid followed by separation of the diastereomeric esters by conventional means (eg. HPLC, chromatography over silica). All stereoisomers are included within the scope of the invention.

Particularly preferred compounds of the invention include:

4,4a,5,6-Tetrahydro-2-(4-methylphenyl)pyrido[3,4-h]cinnolin-3(2H)-one, 2-(4-Chlorophenyl)-4,4a,5,6-tetrahydropyrido[3,4-h]cinnolin-3(2H)-one, 2-(4-Chlorophenyl)-2,4,4a,5,6,7-hexahydropyrido[4', 3':6,7]cyclohepta[1,2-c]pyridazin-3-one, 2-(3,4-Dichlorophenyl)-2,4,4a,5,6,7-hexahydropyrido[4',3':6,7]cyclohepta[1,2-c]-pyridazin-3-one, 2-(3-Chlorophenyl)-4,4a,5,6-tetrahydropyrido[3,4-h]cinnolin-3(2H)-one, 4,4a,5,6-tetrahydro-2-(4-trifluoromethylphenyl)pyrido[3,4-h]cinnolin-3(2H)-one, 2-(4-Chlorophenyl)-4,4a,5,6-tetrahydropyrido[2,3-h]cinnolin-3(2H)-one, 2-(4-Chlorophenyl)-4,4a,5,6-tetrahydropyrido[4,3-h]cinnolin-3(2H)-one, 2-(4-Chlorophenyl)-4,4a,5,6-tetrahydropyrido[3,2-h]cinnolin-3(2H)-one, 2-(4-Chlorophenyl)-2,4,4a,5,6,7-hexahydropyrido[3',2':6,7]cyclohepta[1,2-c]-pyridazin-3-one, 2,3,4,4a,5,6-Hexahydro-2-(4-methylphenyl)pyrido[3,4-h]cinnoline, 2-(3-Chlorophenyl)-2,3,4,4a,5,6-hexahydropyrido[3,4-h]cinnoline, 2-(4-Chlorophenyl)-2,3,4,4a,5,6-hexahydropyrido[3,4-h]cinnoline, 2-(3,4-Dichlorophenyl)-2,4,4a,5,6,7-hexahydro-2H- pyrido[4',3':6,7]cyclohepta[1,2-c]-pyridazine, 2-(4-Chlorophenyl)-2,4,4a,5,6,7-hexahydro-2H-pyrido[4',3':6,7]cyclohepta[1,2-c]-pyridazine,
2-(4-Chlorophenyl)-2,3,4,4a,5,6-hexahydropyrido[2,3-h]cinnoline,
2-(4-Chlorophenyl)-2,3,4,4a,5,6-hexahydropyrido[4,3-h]cinnoline,
5,6-Dihydro-2-(4-methylphenyl)pyrido[3,4-h]cinnolin-3(2H)-one,
2-(4-Chlorophenyl)-5,6-dihydropyrido[2,3-h]cinnolin-3(2H)-one,
2-(4-Chlorophenyl)-5,6-dihydropyrido[4,3-h]cinnolin-3(2H)-one,
2-(4-Chlorophenyl)-5,6-dihydropyrido[3,2-h]cinnolin-3(2H)-one,
2-(4-Chlorophenyl)-2,5,6,7-tetrahydropyrido[4',3':6,7]cyclohepta[1,2-c]pyridazin-3-one,
2-(4-Chlorophenyl)pyrido[2,3-h]cinnolin-3(2H)-one,
2-(4-Chlorophenyl)pyrido[4,3-h]cinnolin-3(2H)-one,
4,4a,5,6-Tetrahydro-2-(4-trifluoromethylphenyl)-2H-pyrido[4,3-h]cinnolin-3-one,
2-(4-Chlorophenyl)-2,3,4,4a,5,6-hexahydro-9-oxidopyrido[4,3-h]cinnoline,
2-(4-Chlorophenyl)-2,3,4,4a,5,6-hexahydro-7-oxidopyrido[2,3-h]cinnoline, and pharmaceutically acceptable derivatives thereof.

According to a further aspect of the invention there is also provided a process for the preparation of compounds of formula I which comprises:

(a) Preparation of a compound of formula I wherein Y is $CH_2$, by reduction of a corresponding compound of formula I wherein Y is C=O, $R^1$ is H and $R^2$ is H or $C_{1-6}$ alkyl.

(b) Preparation of a compound of formula I wherein Y is C=O, X is $(CH_2)_n$ and $R^1$ and $R^2$ together represent a bond, by oxidising a corresponding compound of formula I wherein $R^1$ and $R^2$ represent H.

(c) Preparation of a compound of formula I wherein Y is C=O, X is CH=CH and $R^1$ and $R^2$ together represent a bond, by oxidising a corresponding compound of formula I wherein X is $(CH_2)_2$.

(d) Preparation of a compound of formula I wherein Y is C=O, X is $(CH_2)_n$, $R^1$ is H and $R^2$ is H or $C_{1-6}$ alkyl, by reaction of a compound of formula II:

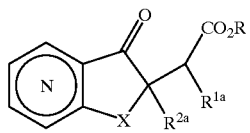

(II)

wherein R is H or $C_{1-3}$ alkyl, $R^{1a}$ is H, $R^{2a}$ is H or $C_{1-6}$ alkyl, and X is X is $(CH_2)_n$, or an acid addition salt thereof, with a hydrazine of formula III:

$Ar^1NHNH_2$ (III)

wherein $Ar^1$ is as hereinbefore defined, or an acid addition salt thereof, and optionally thereafter (a) to (d) forming a pharmaceutically acceptable deivative.

Reaction (a) can be carried out using a suitable reducing agent, for example borane tetrahydrofuran complex under reflux conditions. Reactions (b) and (c) can be carried out using a suitable oxidising agent such as bromine and acetic acid at elevated temperature for example at about 80° C. Reaction (d) is suitably carried out by refluxing in the presence of an appropriate organic solvent (eg xylene).

Compounds of formula II wherein R is H may be prepared by hydrolysis of a corresponding compound of formula II, wherein R is $C_{1-3}$ alkyl, under conditions which are well known to those skilled in the art.

Compounds of formula II wherein R is $C_{1-3}$ alkyl are either known from Synthetic Communications, 24, 273 (1994) or may be prepared analogously to the methods described therein from a compound of formula IV:

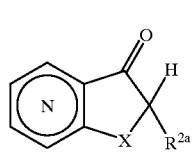

IV wherein $R^{2a}$ and X are as hereinbefore defined.

Compounds of formula IV wherein $R^{2a}$ is $C_{1-6}$ alkyl may be prepared by hydrolysis of a compound of formula V:

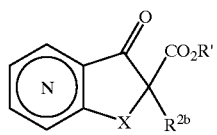

V wherein R' and $R^{2b}$ represent $C_{1-6}$ alkyl, and X is as hereinbefore defined, for example by refluxing in the presence of base (eg. sodium hydroxide) and an appropriate organic solvent (eg. ethanol).

Compounds of formula V may be prepared by reaction of a compound of formula VI:

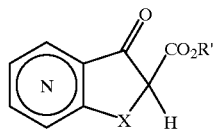

VI wherein X is $(CH_2)_n$ and R' is as hereinbefore defined, with a compound of formula VII:

$R^{2b}Hal$ VII wherein Hal is halogen and $R^{2b}$ is as hereinbefore defined for example at room temperature in the presence of base (eg sodium hydride) and an appropriate organic solvent (eg. tetrahydrofuran).

Compounds of formula VI may be made by reaction of a compound of formula IV, wherein $R^{2a}$ is H with a compound of formula VIII:

$NCCO_2R'$ VIII wherein R' is as hereinbefore defined for example at room temperature or lower, in the presence of a an appropriate base (eg. sodium hydride and a suitable organic solvent (eg. hexamethylphosphoramide).

Compounds of formula IV wherein $R^{2a}$ is H are known from the literature (eg Synthetic Communications, 24, 273 (1994); J. Chem. Soc. Perkin I (1984) 2297; J. Med. Chem. (1991) 34, 2736; and J. Chem. Soc. Perkin Trans. I (1992) 31) or may be prepared analogously to methods described therein.

Compounds of formula III, VII and VIII are either commercially available, well known in the literature or may be prepared conveniently using known techniques It will be appreciated by those skilled in the art that in the process described above the functional groups of intermediate compounds may need to be protected by protecting groups.

Functional groups which it is desirable to protect include hydroxy, amino and carboxylic acid. Suitable protecting groups for hydroxy include organosilyl groups (e.g. tert-butyldimethylsilyl, tert-butyldiphenylsilyl or trimethylsilyl), benzyl and tetrahydropyranyl. Suitable protecting groups for amino include tert-butoxycarbonyl or benzyloxy carbonyl. Suitable protecting groups for carboxylic acid include $C_{1-6}$ alkyl or benzyl esters. The protection and deprotection of functional groups may take place before or after a reaction step.

The use of protecting groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wutz, Wiley-Interscience (1991).

According to the invention there is further provided the compounds of the invention for use in therapy as pharmaceuticals. In particular the compounds of the invention possess antiallergic and antiinflammatory activity, for example as shown in the tests described below.

The compounds of the invention are thus indicated for use in the treatment of allergic and inflammatory diseases of the airways such as asthma (e.g. bronchial asthma, allergic asthma, intrinsic asthma, extrinsic asthma and dust asthma), particularly chronic or inveterate asthma (e.g. late asthma and airway hyper-responsiveness), bronchitis and the like.

Further, the compounds of the invention are indicated in the treatment of diseases including inflammations/allergies such as rhinitis, including all conditions characterised by inflammation of the nasal mucus membrane, such as acute rhinitis, allergic rhinitis, atrophic rhinitis, chronic rhinitis including rhinitis caseosa, hypertrophic rhinitis, rhinitis purulenta and rhinitis sicca, rhinitis medicamentosa, membranous rhinitis including croupous, fibrinous and pseudomembranous rhinitis, scrofoulous rhinitis, seasonal rhinitis including rhinitis nervosa (hay fever) and vasomotor rhinitis.

The compounds of the invention are also indicated for use in the treatment of chronic allergic disorders, atopic dermatitis, cutaneous eosinophilias, eosinophilic fascitis, hyper IgE syndrome, vernal conjunctivitis, systemic lupus erythematosis, thyroiditis, lepromatous leprosy, sezary syndrome, chronic graft versus host disease, myasthenia gravis, idiopathic thrombocytopenia pupura and the like.

The compounds of the invention may also have activity in both the prophylactic and therapeutic treatment of acquired immunodeficiency syndrome (AIDS), the prevention of chronic rejection of allografts mediated by humoral immunity, and in the treatment of autoimmune diseases such as multiple sclerosis and rheumatoid arthritis.

Of particular interest amongst the above indications are the use of the compounds of the invention in asthma, especially the prophylaxis of asthma, and in rhinitis, most particularly allergic rhinitis and seasonal rhinitis including rhinitis nervosa (hay fever).

According to a further aspect of the present invention, there is provided a method of treatment or prophylaxis of an allergic or an inflammatory disorder, which method comprises administration of a therapeutically effective amount of a compound of formula I as hereinbefore defined, or a pharmaceutically acceptable derivative thereof, to a person suffering from, or susceptible to such a disease.

The invention further provides the use of a compound of formula (I) or a pharmaceutically acceptable derivative thereof in the manufacture of a medicament for the treatment or prophylaxis of the above disorders, in particular asthma and rhinitis.

Administration of the compounds of the invention may be topical (for example by inhalation to the lung). The compounds of the invention may be inhaled as a dry powder which may be pressurized or non-pressurized.

In non-pressurized powder compositions, the active ingredient in finely divided form may be used in admixture with a larger sized pharmaceutically acceptable inert carrier The composition may alternatively be pressurized and contain a compressed gas, e.g. nitrogen, or a liquefied gas propellant. In such pressurized compositions, the active ingredient is preferably finely divided. The pressurized composition may also contain a surface active agent. The pressurized compositions may be made by conventional methods.

The compounds of the invention may be administered systemically (for example by oral administration to the gastrointestinal tract). The active ingredient may be formulated together with known adjuvants, diluents or carriers using conventional techniques to produce tablets or capsules for oral administration to the gastrointestinal tract.

Examples of suitable adjuvants, diluents or carriers for oral administration in the form of tablets, capsules and dragees include microcrystalline cellulose, calcium phosphate, diatomaceous earth, a sugar such as lactose, dextrose or mantel, talc, stark acid, starch, sodium bicarbonate and/or gelatine.

According to a further aspect of the invention there is provided a pharmaceutical composition comprising a compound of formula I as hereinbefore defined or a pharmaceutically acceptable derivative thereof, in association with a pharmaceutically acceptable adjuvant, diluent or carrier.

Suitable doses for administration topical or orally are in the range 0.01 to 30 mgkg$^{-1}$ day$^{-1}$, for example 0.3 mgkg$^{-1}$ day$^{-1}$.

It will be understood by those skilled in the art that certain functional groups in the compounds of the invention may be protected using appropriate protecting groups to form "protected derivatives" of the compounds of the invention. It will also be appreciated that, although such protected derivatives may not possess pharmacological activity as such, they may be administered and thereafter metabolised in the body to form the compound of the invention which is pharmacologically active. Such derivatives may therefore be described as "prodrugs". All protected derivatives and prodrugs of compounds of formula I are included within the scope of the invention.

The invention is illustrated by the following examples.

EXAMPLE 1

4,4a,5,6-Tetrahydro-2-(4-methylphenyl)pyrido[3,4-h]cinnolin-3(2H)-one

Methyl 5,6,7,8-tetrahydro-5-oxoisoquinoline-6-acetate hydrobromide (1.2 g) (Wu et al, Synthetic Communications 24, 273 (1994)) 4-tolylhydrazine (0.5 g) and 4-tolylhydrazine hydrochloride (0.19 g) in xylene (20 ml) were heated under reflux for 3 hours. The reaction mixture was allowed to cool to room temperature and the volatiles removed. The residue was dissolved in dichloromethane-methanol, washed with sodium hydrogen carbonate solution twice and then brine. The organic phase was dried, filtered and concentrated to a dark oil. The crude product was adsorbed onto silica and chromatographed eluting with 7:3 dichloromethane:ethyl acetate. The resultant oil was triturated with ether and recrystallised from isopropanol to give the title compound (0.3 g).

mp 152–153° C.; M⁺291 (EI).; ¹H NMR (CDCl₃) δ: 1.70 (m, 1H); 2.30 (m, 1H); 2.39 (s, 3H); 2.50 (t, 1H); 2.85 (m, 2H); 3.00 (m, 2H); 7.25 (d, 2H); 7.40 (d, 2H); 7.90 (d, 1H); 8.47 (d, 1H); 8.50 (s, 1H).

EXAMPLE 2
2-(4-Chlorophenyl)-4,4a,5,6-tetrahydropyrido[3,4-h]cinnolin-3(2H)-one Prepared according to the method described in Example 1 from methyl 5,6,7,8-tetrahydro-5-oxoisoquinoline-6-acetate hydrobromide and 4-chlorophenylhydrazine.

mp 103–104° C.; (M+H)⁺312/314 (ESI).; ¹H NMR (CDCl₃) δ: 1.72 (dt,1H); 2.36 (dt,1H); 2.51 (t,1H); 2.85 (dt,1H); 2.95 (dd,1H); 3.05 (m,2H); 7.42 (d,2H); 7.53 (d,2H); 7.92 (d,1H); 8.50 (dd,1H); 8.53 (d,1H).

EXAMPLE 3
2-(4-Chlorophenyl)-2,4,4a,5,6,7-hexahydropyrido[4',3':6,7]cyclohepta[1,2-c]pyridazin-3-one Prepared according to the method described in Example 1 from 9-oxo-6,7,8,9-tetrahydro-5H-cyclohepta[c]pyridine-8-acetic acid (prepared by hydrolysis of the corresponding ketal, the latter being prepared from 5,6,7,8-tetrahydrocyclohepta[c]pyridine-9-one (Hicks et al, J. Chem. Soc. Perkin I (1984)2297) according to the method of Wu et al supra) and 4-chlorophenylhydrazine.

mp 133–134° C.; M⁺325/327 (EI).; ¹H NMR (d₆-DMSO) δ: 1.48 (m,1H); 1.75 (m, 2H); 1.90 (m, 1H); 2.49–2.94 (m, 4H); 3.21 (m, 1H) ; 7.30 (d, 1H); 7.48 (d, 2H); 7.62 (d, 2H); 8.52 (d, 1H); 8.70 (s, 1H).

EXAMPLE 4
2-(3,4-Dichlorophenyl)-2,4,4a,5,6,7-hexahydropyrido[4',3':6,7]cyclohepta[1,2-c]-pyridazin-3-one hydrochloride Prepared according to the method described in Example 1 from 9-oxo-6,7,8,9-tetrahydro-5H-cyclohepta[c]pyridine-8-acetic acid and 4-chlorophenylhydrazine, the compound being dissolved in ether and hydrogen chloride in dioxan added to precipitate the hydrochloride salt.

mp 197–202° C.; M⁺359/361/363 (EI).; ¹H NMR (DMSO): δ 1.50 (m, 1H); 1.75 (m, 2H); 1.95 (m, 1H); 2.64 (m, 1H); 2.78 (m, 1H); 3.00 (m, 2H); 3.30 (m, 1H); 7.68 (m, 3H); 7.93 (d, 1H); 8.73 (d, 1H); 8.89 (s, 1H)

EXAMPLE 5
2-(3-Chlorophenyl)-4,4a,5,6-tetrahydropyrido[3,4-h]cinnolin-3(2H)-one Prepared according to the method described in Example 1 from methyl 5,6,7,8-tetrahydro-5-oxoisoquinoline-6-acetate hydrobromide and 3-chlorophenylhydrazine.

mp 153–153.5° C.; M⁺311/313 (EI).; ¹H NMR (DMSO d-6) δ 1.61 (qd, 1H), 2.21 (m, 1H), 2.62–2.75 (m, 2H), 2.82 (dd, 1H) 2.95 (dt, 1H), 3.17 (m, 1H), 7.39 (dt, 1H), 7.49 (t, 1H), 7.57 (dt, 1H), 7.66 (t, 1H), 7.87 (d, 1H), 8.47 (d, 1H) and 8.55 (s, 1H).

EXAMPLE 6
4,4a,5,6-tetrahydro-2-(4-trifluoromethylphenyl)pyrido[3,4-h]cinnolin-3(2H)-one Prepared according to the method described in Example 1 from methyl 5,6,7,8-tetrahydro-5-oxoisoquinoline-6-acetate hydrobromide and 4-trifluoromethylphenylhydrazine.

mp 144–7° C.; (M+H)⁺346 (ESI).; ¹H NMR (CDCl₃) δ: 1.7 (dq,1H); 2.4 (m,1H); 2.5 (t,1H); 2.8 to 3.1 (m,4H); 7.7 (m,4H); 8.0 (d,1H); 8.5 (m,2H).

EXAMPLE 7
2-(4-Chlorophenyl)-4,4a,5,6-tetrahydropyrido[2,3-h]cinnolin-3(2H)-one Prepared according to the method described in Example 1 from methyl 5,6,7,8-tetrahydro-5-oxoquinoline-6-acetate (prepared from 7,8-dihydroquinoline-5(6H)-one (J. Med. Chem. (1991)34, 2736) according to the method of Wu et al supra) and 4-chlorophenylhydrazine.

mp 178–180° C.; M⁺311/313 (EI); ¹H NMR (CDCl₃) δ: 1.80 (dq,1H); 2.40 (m,1H); 2.51 (t,1H); 2.9–3.1 (m,3H); 3.20 (dt,1H); 7.22 (dd,1H); 7.40 (d,2H); 7.56 (d,2H); 8.41 (d,1H); 8.55 (d,1H).

EXAMPLE 8
2-(4-Chlorophenyl)-4,4a,5,6-tetrahydropyrido[4,3-h]cinnolin-3(2H)-one Prepared according to the method described in Example 1 from methyl 5,6,7,8, -tetrahydro-8-oxoisoquinoline-7-acetate (prepared from 5,6-dihydroquinoline-8(7H)-one (Boyd et al, J. Chem. Soc., Perkin Trans. I (1992)31) according to the method of Wu et al supra) and 4-chlorophenylhydrazine.

mp 166–168° C.; (M+H)⁺312/314 (ESI).; ¹H NMR (CDCl₃) δ: 1.75 (m, 1H); 2.30 (m, 1H); 2.50 (t, 1H); 2.90–3.05 (m, 4H); 7.10 (d, 1H); 7.40 (d, 2H); 7.60 (d, 2H); 8.50 (d, 1H); 9.33 (s, 1H).

EXAMPLE 9
2-(4-Chlorophenyl)-4,4a,5,6-tetrahydropyrido[3,2-h]cinnolin-3(2H)-one Prepared according to the method described in Example 1 from methyl 5,6,7,8-tetrahydro-8-oxoquinoline-7-acetate (prepared from 6,7-dihydroquinoline-8(5H)-one according to the method of Wu et al supra) and 4-chlorophenylhydrazine.

mp 174–175° C.; M⁺311/313 (EI).; ¹H NMR (CDCl₃) δ: 1.75 (m, 1H); 2.30 (m, 1H); 2.55 (t, 1H); 2.90 (dd, 1H); 2.95 (m, 2H); 3.15 (m, 1H); 7.25 (1H); 7.40 (dd, 2H); 7.55 (m, 3H); 8.65 (d, 1H).

EXAMPLE 10
2-(4-Chlorophenyl)-2,4,4a,5,6,7-hexahydropyrido[3',2':6,7]cyclohepta[1,2-c]-pyridazin-3-one Prepared according to the method described in Example 1 from 9-oxo-6,7,8,9-tetrahydro-5H-cyclohepta[c]pyridine-9-acetic acid (prepared by hydrolysis of the corresponding ketal, the latter being known from Wu et al reference supra) and 4-chlorophenylhydrazine.

mp 167–168° C.; (M+H)⁺326/328 (ESI).; ¹H NMR (DMSO) δ: 1.60 (m,1H); 1.80 (m,2H); 2.65 (m,1H); 2.80 (m,3H); 3.15 (m,2H); 7.39 (m,1H); 7.47 (d,2H); 7.56 (d,2H); 7.70 (d,1H); 8.49 (d,1H).

EXAMPLE 11
2,3,4,4a,5,6-Hexahydro-2-(4-methylphenyl)pyrido[3,4-h]cinnoline 4,4a,5,6-Tetrahydro-2-(4-methylphenyl)pyrido[3,4-h]cinnolin-3(2H)-one (0.14 g; from Example 1 above) was placed in a flask under nitrogen. Borane tetrahydofuran complex (1M, 2.4 ml) was added and the solution warmed to room temperature for 3.5 hours. Methanol (5 ml) was added. Water was added and the aqueous solution extracted thrice with ethyl acetate. The organics were washed with sodium hydrogen carbonate (saturated solution), and brine then dried, filtered and concentrated to give a yellow solid. The solid was adsorbed onto silica then chromatographed eluting with first 7:3 dichloromethane:ethyl acetate, then ethyl acetate to give a yellow solid. Recrystallisation from ethyl acetate/hexane gave the title compound (30 mg)

mp 158–159° C.; M⁺277 (EI).; ¹H NMR (CDCl₃) δ: 1.55 (td, 1H); 1.75 (m, 1H); 2.20 (m, 2H); 2.30 (s, 3H); 2.45 (m,

1H); 2.90 (m, 2H); 3.50 (td, 1H); 4.05 (m, 1H); 7.15 (d, 2H); 7.25 (d, 2H); 7.90 (d, 1H); 8.37 (d, 2H)

EXAMPLE 12
2-(3-Chlorophenyl)-2,3,4,4a,5,6-hexahydropyrido[3,4-h]cinnoline 2-(3-Chlorophenyl)-4,4a,5,6-tetrahydropyrido[3,4-h]cinnolin-3(2H)-one (from Example 5 above; 66 mg) was placed in a flask under nitrogen. Borane tetrahydrofuran complex (1.0M in THF; 3 ml) was added and the solution stirred for 16 hours at ambient temperature. The mixture was added to methanol (3 ml) with stirring and then concentrated hydrochloric acid (0.5 ml) was added cautiously. The mixture was heated under reflux for 30 minutes, then cooled to room temperature and the volatiles removed on a rotary evaporator. The resultant product was partitioned between $NaHCO_3$ (aqueous) and ethyl acetate. The aqueous phase was extracted twice more with ethyl acetate. The combined organic layers were washed with brine, dried, filtered and concentrated to give a solid which was chromatographed eluting with ethyl acetate to give a solid which was recrystallised from isopropanol to yield the title compound as yellow crystals (14 mg).

mp 152–155° C.; MS (ESI) 298/300 (M+H).; $^1$H NMR (DMSO d-6) δ 1.44 (qd, 1H), 1.63 (qd, 1H), 2.16 (m, 1H), 2.23 (m, 1H), 2.52 (m, 1H), 2.77–2.90 (m, 2H), 3.47 (td, 1H), 4.10 (m, 1H), 6.93 (m, 1H), 7.30–7.33 (m, 2H), 7.39 (s, 1H), 7.85 (d, 1H), 8.37 (d, 1H) and 8.40 (s, 1H)

EXAMPLE 13
2-(4-Chlorophenyl)-2,3,4,4a,5,6-hexahydropyrido[3,4-h]cinnoline

Prepared according to the method described in Example 12 from 2-(4-chlorophenyl)-4,4a,5,6-tetrahydropyrido[3,4-h]cinnolin-3(2H)-one (from Example 2 above).

mp 190–191° C.; (M+H)$^+$292/300 (ESI).; $^1$H NMR (DMSO) δ: 1.40 (dq,1H); 1.80 (dq,1H); 2.15 (m,1H); 2.20 (m,1H); 2.80 (m,2H); 3.45 (dt,1H); 4.07 (d,1H); 7.36 (q,4H); 7.85 (d,1H); 8.35 (d,1H); 8.38 (s,1H).

EXAMPLE 14
2-(3,4-Dichlorophenyl)-2,4,4a,5,6,7-hexahydro-2H-pyrido[4',3':6,7]cyclohepta[1,2-c]-pyridazine Prepared according to the method described in Example 12 from 2-(3,4-dichlorophenyl)-2,4,4a,5,6,7-hexahydro-pyrido[4',3':6,7]cyclohepta[1,2-c]-pyridazin-3-one (Example 4 above).

mp 156–157° C.; (M+H)$^+$346/348/350 (ESI).; $^1$H NMR (CDCl$_3$): δ 1.70 (m, 1H); 1.87 (m, 2H); 1.93 (m, 2H); 2.13 (m, 1H); 2.59 (m, 1H); 2.80 (m, 1H); 2.94 (m, 1H); 3.52 (m, 1H); 3.78 (m, 1H); 7.04 (d, 1H); 7.16 (dd, 1H); 7.32 (d, 1H); 7.38 (d, 1H); 8.41 (d, 1H); 8.85 (s, 1H).

EXAMPLE 15
2-(4-Chlorophenyl)-2,4,4a,5,6,7-hexahydro-2H-pyrido[4',3':6,7]cyclohepta[1,2-c]-pyridazine Prepared according to the method described in Example 12 from 2-(4-chlorophenyl)-2,4,4a,5,6,7-hexahydro-pyrido[4',3':6,7]cyclohepta[1,2-c]-pyridazin-3-one (from Example 3 above).

mp 135–136° C.; (M+H)$^+$312/314 (ESI).; $^1$H NMR (d$_6$-DMSO) δ;1.61 (m, 1H); 1.75–1.88 (m, 4H); 2.03 (m, 1H); 2.64 (m, 1H); 2.76 (m, 1H); 2.96 (m, 1H); 3.52 (m, 1H); 3.84 (m, 1H); 7.19 (d, 1H), 7.31 (s, 4H); 8.36 (d, 1H); 8.73 (s, 1H).

EXAMPLE 16
2-(4-Chlorophenyl)-2,3,4,4a,5,6-hexahydropyrido[2,3-h]cinnoline

Prepared according to the method described in Example 12 from 2-(4-chlorophenyl)-4,4a,5,6-tetrahydropyrido[2,3-h]cinnolin-3(2H)-one (from Example 7 above).

mp 142–143° C.; M$^+$297/299 (EI); $^1$H NMR (DMSO) δ: 1.55 (dq,1H); 1.65 (dq,1H); 2.20 (m,1H); 2.30 (m,1H); 2.55 (m,1H); 2.95 (m,2H); 3.40 (dt,1H); 4.07 (d,1H); 7.24 (dd, 1H); 7.30 (q,4H); 8.33 (d,1H); 8.38 (d,1H).

EXAMPLE 17
2-(4-Chlorophenyl)-2,3,4,4a,5,6-hexahydropyrido[4,3-h]cinnoline

Prepared according to the method described in Example 12 from 2-(4-chlorophenyl)-4,4a,5,6-tetrahydropyrido[4,3-h]cinnolin-3(2H)-one (from Example 8 above).

mp 170–172° C.; M$^+$297/299 (EI).; $^1$H NMR (CDCl$_3$) δ: 1.55 (m, 1H); 1.80 (m, 1H); 2.20 (m, 1H); 2.25 (m, 1H); 2.45 (m, 1H); 2.90 (m, 2H); 3.50 (m, 1H); 4.00 (m, 1H); 7.00 (d, 1H); 7.26 (br s, 4H); 8.30 (d, 1H); 9.30 (s, 1H).

EXAMPLE 18
5,6-Dihydro-2-(4-methylphenyl)pyrido[3,4-h]cinnolin-3(2H)-one 4,4a,5,6-Tetrahydro-2-(4-methylphenyl)pyrido[3,4-h]cinnolin-3(2H)-one (0.14 g; from Example 1 above) was dissolved in acetic acid (2 ml) and heated to 80° C. Bromine (0.027 ml) was added dropwise and the solution stirred for 16 hours. The reaction was cooled to room temperature, poured into aqueous sodium hydrogen carbonate and extracted thrice with dichloromethane. The organics were washed with sodium thiosulphate solution and brine, dried, filtered and concentrated. The product was adsorbed onto silica then chromatographed eluting with 1:1 dichloromethane:ethyl acetate then recrystallised from isopropanol twice to give the title compound (35 mg).

mp 188–189° C.; (M+H)$^+$290 (ESI).; $^1$H NMR (CDCl$_3$) δ: 2.40 (s, 3H); 3.00 (s, 4H); 6.90 (s, 1H); 7.30 (d, 2H); 7.55 (d, 2H); 7.88 (d, 1H); 8.55 (d, 2H).

EXAMPLE 19
2-(4-Chlorophenyl)-5,6-dihydropyrido[2,3-h]cinnolin-3(2H)-one

Prepared according to the method described in Example 18 from 2-(4-chlorophenyl)-4,4a,5,6-tetrahydropyrido[2,3-h]cinnolin-3(2H)-one (from Example 7 above). mp 166–167° C.

M$^+$309/311 (EI).; $^1$H NMR (CDCl$_3$) δ: 3.04 (t,2H); 3.19 (t,2H); 6.92 (s,1H); 7.30 (dd,1H); 7.46 (d,2H); 7.65 (d,2H); 8.33 (d, 1H); 8.60 (d, 1H). The product of further oxidation, 2-(4-chlorophenyl)pyrido[2,3-h]cinnolin-3(2H)-one was also isolated from this reaction.

EXAMPLE 20
2-(4-Chlorophenyl)-5,6-dihydropyrido[4,3-h]cinnolin-3(2H)-one

Prepared according to the method described in Example 18 from 2-(4-chlorophenyl)-4,4a,5,6-tetrahydropyrido[4,3-h]cinnolin-3(2H)-one (from Example 8 above). mp 166–168° C.

(M+H)$^+$310/312 (ESI).; $^1$H NMR (CDCl$_3$) δ: 3.00 (br s, 4H); 6.90 (s, 1H); 7.20 (d, 1H); 7.50 (d, 2H); 7.70 (d, 2H); 8.55 (d, 1H); 9.23 (s, 1H). The product of further oxidation, 2-(4-chlorophenyl)pyrido[4,3-h]cinnolin-3(2H)-one, was also isolated from this reaction.

EXAMPLE 21
2-(4-Chlorophenyl)-5,6-dihydropyrido[3,2-h]cinnolin-3(2H)-one

Prepared according to the method described in Example 18 from 2-(4-chlorophenyl)-4,4a,5,6-tetrahydropyrido[3,2- h]cinnolin-3(2H)-one (from Example 9 above). mp 174–176° C. M+309/311 (EI).; $^1$H NMR (CDCl$_3$) δ: 2.98–3.04 (m, 4H); 6.92 (s, 1H); 7.30 (td, 1H); 7.45 (d, 2H); 7.65 (m, 3H); 8.70 (dd, 1H).

EXAMPLE 22

2-(4-Chlorophenyl)-2,5,6,7-tetrahydropyrido[4',3':6,7]cyclohepta[1,2-c]pyridazin-3-one Prepared according to the method described in Example 18 from 2-(4-chlorophenyl)-2,4,4a,5,6,7-hexahydro-pyrido[4',3':6,7]cyclohepta[1,2-c]pyridaz-3-one (from Example 3 above).

mp 172–174° C.; M+323/325 (EI).; $^1$H NMR (d$_6$-DMSO) δ: 2.11 (q, 2H); 2.46 (t, 2H); 2.71 (t, 2H); 7.08 (s, 1H); 7.40 (d, 1H); 7.57 (d, 2H); 7.76 (d, 2H); 8.59 (d, 1H); 8.69 (s).

EXAMPLE 23

2-(4-Chlorophenyl)pyrido[2,3-h]cinnolin-3(2H)-one

The by-product of Example 19 was purified further and characterised.

mp 283–285° C.; M+307/309 (EI); $^1$H NMR (DMSO) δ: 7.55 (s,1H); 7.65 (m,2H); 7.68 (d,2H); 7.72 (d,1H); 7.85 (d,2H); 8.83 (dd, 1H); 8.90 (dd, 1H).

EXAMPLE 24

2-(4-Chlorophenyl)pyrido[4,3-h]cinnolin-3(2H)-one

The by-product of Example 20 was purified further and characterised.

mp 259–265° C.; (M+H)+308/310 (ESI).; $^1$H NMR (CDCl$_3$) δ: 7.25 (s, 1H); 7.35 (d, 1H); 7.45 (d, 1H); 7.50 (d, 1H); 7.54 (d, 2H); 7.80 (dd, 2H); 8.80 (dd, 1H); 9.80 (s, 1H).

EXAMPLE 25

4,4a,5,6-Tetrahydro-2-(4-trifluoromethylphenyl)-2H-pyrido[4,3-h]cinnolin-3-one

Methyl 5,6,7,8-tetrahydro-8-oxoisoquinolin-7-acetate (1.0 g), 4-trifluoromethyl-phenylhydrazine (1.6 g) and para-toluenesulphonic acid (0.25 g) were heated under reflux in xylene (20 ml) for 4 hours. The cooled reaction was poured into 2M sodium hydroxide solution and extracted with ethyl acetate, which was then washed with brine, dried, and evaporated to a gum. The gum was chromatographed on silica gel, eluting with ethyl acetate-isohexane (1:1), to afford a solid which was crystallised from isopropanol-isohexane to yield the title compound (0.25 g), mp 141–142° C.; MS APCI(+ve) 346 (M+1); $^1$H NMR (CDCl$_3$) δ: 1.73 (dt,1H); 2.3 (m,1H); 2.55 (t, J=15.9 Hz, 1H); 2.9–3.05 (m, 4H); 7.14 (d, 1H); 7.69 (d, 2H); 7.81 (d, 2H); 8.51 (d, 1H); 9.63 (s, 1H).

EXAMPLE 26

2-(4-Chlorophenyl)-2,3,4,4a,5,6-hexahydro-9-oxidopyrido[4,3-h]cinnoline

3-Chloroperoxybenzoic acid (60%) (35 mg) was added to a solution of 2-(4-Chlorophenyl)-2,3,4,4a,5,6-hexahydropyrido[4,3-h]cinnoline (example 17, 25 mg) in dichloromethane (5 ml) at 25° C. After 4 hours the reaction was diluted with dichloromethane and sequentially washed with an aqueous solution of sodium metabisulfite, saturated sodium bicarbonate solution, brine, dried and evaporated. Purification by chromatography, eluting with ethyl acetate/methanol (4:1) afforded the title compound (19 mg).

mp 216° C. (dec); MS APCI(+ve) 314/316 (M+1); $^1$H NMR (DMSO) δ: 1.42 (dq,1H); 1.63 (dq,1H); 2.12 (d,1H); 2.24 (d,1H); 2.7–2.9 (m, 3H); 3.45 (dt,1H); 4.08 (dd,1H); 7.24 (d, 1H); 7.35 (s,4H); 7.99 (d, 1H); 8.44 (s, 1H)

EXAMPLE 27

2-(4-Chlorophenyl)-2,3,4,4a,5,6-hexahydro-7-oxidopyrido[2,3-h]cinnoline

3-Chloroperoxybenzoic acid (60%) (35 mg) was added to a solution of 2-(4-Chlorophenyl)-2,3,4,4a,5,6-hexahydropyrido[2,3-h]cinnoline (example 16, 25 mg) in dichloromethane (5 ml) at 25° C. After 4 hours the reaction was diluted with dichloromethane and sequentially washed with an aqueous solution of sodium metabisulfite, saturated sodium bicarbonate solution, brine, dried and evaporated. Purification by chromatography, eluting with ethyl acetate/methanol (4:1) afforded the title compound (17 mg).

mp 202° C. (dec); MS APCI(+ve) 314/316 (M+1); $^1$H NMR (DMSO) δ: 1.44 (dq,1H); 1.64 (dq,1H); 2.20 (m,2H); 2.7–2.9 (m, 3H); 3.41 (dt, 1H); 4.08 (dt,1H); 7.29 (t, 1H); 7.34 (q,4H); 7.89 (d, 1H); 8.21 (d, 1H). 3 protons not seen, distortions at edge of DMSO and H$_2$O signals suggest their location.

Pharmacological Data

Test A—Chronic graft-versus-host test

Pharmacological activity of the compounds of the invention may be demonstrated using the method of J M Doutrelepont et al ([Clin Exp Immunol, 1991, vol 83, 133–6; Inhibition of chronic graft-versus-host (c-GVH) disease in the mouse]. Test compound was administered to mice subcutaneously as a suspension in saline with TWEEN-80 every day for 21 days.

2-(4-Chlorophenyl)-4,4a,5,6-tetrahydropyrido[4,3-h]cinnolin-3(2H)-one was found to inhibit IgE production by 45% at a single dose of 10 mgkg$^{-1}$. 2-(4-Chlorophenyl)-2,3,4,4a,5,6-hexahydropyrido[2,3-h]cinnoline was found to inhibit IgE production by 58% at a single dose of 10 mgkg$^{-1}$.

Test B—Inhibition of Eosinophilia

The effects of the compounds of the invention on inflammatory cells in mouse lungs was assessed by the following method, adapted from Brusselle et al , Clin. Exp. Allergy 1994, 24, 73–80. The measurement of eosinophil peroxidase as a marker for eosinophil numbers was adapted from Cheng et al, J. Pharmacol Exp. Ther. 1993, 264, 922–929.

Male Balb/c mice were sensitised to ovalbumin/Al(OH)$_3$ mixture. Fourteen days after sensitisation dosing with compound commenced. Compound was administered daily either orally or subcutaneously as a suspension or solution (depending on dose and compound solubility) in 5% Tween 80.

17 days after sensitisation and one hour after the fourth dose of compound, the mice were placed in perspex chambers into which a solution of ovalbumin (2% w/v) was nebulised. The mice were allowed to inhale the ovalbumin for a period of 30–40 min. This challenge was repeated daily at the same time for a further 3 or 7 days.

In the case of the 4 day challenge, on the final day of dosing an additional challenge with ovalbumin was given 4 hours after the first.

The following day the animals were sacrificed and inhibition of the following parameters was measured by comparison to control animals:

(1) Increase in the numbers of inflammatory cells in the bronchioalveolar lavage, in particular eosinophils (after the 4 day dosing).

(2) Accumulation of eosinophils within lung tissue, as measured by the increase in eosinophil peroxidase activity in homogenised lung tissue (after the 8 day dosing).

(3) Increase in antibody titres (IgE, IgGl and IgG2a) present in the serum obtained from whole blood (after the 8 day dosing).

Certain compounds of the invention show activities in the chronic graft versus host test and the inhibition of eosinophilia test with ED$_{50}$'s in the range of 0.1–10 mg/kg.

We claim:

1. A compound of formula I:

(I)

wherein
X is $(CH_2)n$ or $CH=CH$;
n is 1, 2 or 3;
Y is $CH_2$ or $C=O$;
$R^1$ is hydrogen or together with $R^2$ is a carbon—carbon bond;
$R^2$ is hydrogen, $C_{1-6}$ alkyl or together with $R^1$ is a carbon-carbon bond; and
$Ar^1$ represents thiazolyl, phenyl, pyridyl, pyrimidinyl, 2-benzothiazolyl, 2- or 3-quinolyl or 2-quinoxalinyl all of which are optionally substituted by one or more substituents selected from halo, nitro, cyano, phenyl, phenylsulfonyl, $C_{1-6}$ alkyl, $C_{1-6}$ alkoxy, $C_{1-6}$ alkylthio, $C_{1-6}$ alkylsulfinyl, COOH, COO($C_{1-6}$ alkyl), $CONH_2$, $C_{1-6}$ alkyl substituted by phenyl, or phenyl, in which any alkyl, alkoxy, alkylthio and alkylsulfinyl groups may optionally be substituted by one or more fluorine atoms;
provided that when Y is $CH_2$, $R^1$ and $R^2$ do not together represent a bond; and pharmaceutically acceptable derivatives thereof.

2. A compound according to claim 1 in which X is $(CH_2)_n$.

3. A compound according to claim 1 in which Y is $C=O$.

4. A compound according to claim 1 in which $R^1$ is hydrogen.

5. A compound according to claim 1 in which $R^2$ is hydrogen.

6. A compound according to any one of claims 1 to 5 in which $Ar^1$ is phenyl optionally substituted by one or more substituents selected from $C_{1-6}$ alkyl, halogen, nitro, cyano or $CF_3$.

7. A compound according to claim 1 which is:
4,4a,5,6-Tetrahydro-2-(4-methylphenyl)pyrido[3,4-h]cinnolin-3(2H)-one,
2-(4-Chlorophenyl)-4,4a,5,6-tetrahydropyrido[3,4-h]cinnolin-3(2H)-one,
2-(4-Chlorophenyl)-2,4,4a,5,6,7-hexahydropyrido[4',3':6,7]cyclohepta[1,2-c]pyridazin-3-one,
2-(3,4-Dichlorophenyl)-2,4,4a,5,6,7-hexahydropyrido[4',3':6,7]cyclohepta[1,2-c]-pyridazin-3-one,
2-(3-Chlorophenyl)-4,4a,5,6-tetrahydropyrido[3,4-h]cinnolin-3(2H)-one,
4,4a,5,6-tetrahydro-2-(4-trifluoromethylphenyl)pyrido[3,4-h]cinnolin-3(2H)-one,
2-(4-Chlorophenyl)-4,4a,5,6-tetrahydropyrido[2,3-h]cinnolin-3(2H)-one,
2-(4-Chlorophenyl)-4,4a,5,6-tetrahydropyrido[4,3-h]cinnolin-3(2H)-one,
2-(4-Chlorophenyl)-4,4a,5,6-tetrahydropyrido[3,2-h]cinnolin-3(2H)-one,
2-(4-Chlorophenyl)-2,4,4a,5,6,7-hexahydropyrido[3',2':6,7]cyclohepta[1,2-c]-pyridazin-3-one,
2,3,4,4a,5,6-Hexahydro-2-(4-methylphenyl)pyrido[3,4-h]cinnoline,
2-(3-Chlorophenyl)-2,3,4,4a,5,6-hexahydropyrido[3,4-h]cinnoline,
2-(4-Chlorophenyl)-2,3,4,4a,5,6-hexahydropyrido[3,4-h]cinnoline,
2-(3,4-Dichlorophenyl)-2,4,4a,5,6,7-hexahydro-2H- pyrido[4',3':6,7]cyclohepta[1,2-c]-pyridazine,
2-(4-Chlorophenyl)-2,4,4a,5,6,7-hexahydro-2H-pyrido[4',3':6,7]cyclohepta[1,2-c]-pyridazine,
2-(4-Chlorophenyl)-2,3,4,4a,5,6-hexahydropyrido[2,3-h]cinnoline,
2-(4-Chlorophenyl)-2,3,4,4a,5,6-hexahydropyrido[4,3-h]cinnoline,
5,6-Dihydro-2-(4-methylphenyl)pyrido[3,4-h]cinnolin-3(2H)-one,
2-(4-Chlorophenyl)-5,6-dihydropyrido[2,3-h]cinnolin-3(2H)-one,
2-(4-Chlorophenyl)-5,6-dihydropyrido[4,3-h]cinnolin-3(2H)-one,
2-(4-Chlorophenyl)-5,6-dihydropyrido[3,2-h]cinnolin-3(2H)-one,
2-(4-Chlorophenyl)-2,5,6,7-tetrahydropyrido[4',3':6,7]cyclohepta[1,2-c]pyridazin-3-one,
2-(4-Chlorophenyl)pyrido[2,3-h]cinnolin-3(2H)-one,
2-(4-Chlorophenyl)pyrido[4,3-h]cinnolin-3(2H)-one,
4,4a,5,6-Tetrahydro-2-(4-trifluoromethylphenyl)-2H-pyrido[4,3-h]cinnolin-3-one,
2-(4-Chlorophenyl)-2,3,4,4a,5,6-hexahydro-9-oxidopyrido[4,3-h]cinnoline,
2-(4-Chlorophenyl)-2,3,4,4a,5,6-hexahydro-7-oxidopyrido[2,3-h]cinnoline, and pharmaceutically acceptable derivatives thereof.

8. A pharmaceutical composition comprising a compound of formula I or a pharmaceutically acceptable derivative thereof as defined in claims 1 in association with a pharmaceutically acceptable adjuvant, diluent or carrier.

9. A process for the preparation of compounds of formula I which comprises:
(a) Preparation of a compound of formula I as defined in claim 1 wherein Y is $CH_2$, by reduction of a corresponding compound of formula I wherein Y is $C=O$, $R^1$ is H and $R^2$ is H or $C_{1-6}$ alkyl,
(b) Preparation of a compound of formula I as defined in claim 1 wherein Y is $C=O$, X is $(CH_2)_n$ and $R^1$ and $R^2$ together represent a bond, by oxidizing a corresponding compound of formula I wherein $R^1$ and $R^2$ represent H,
(c) Preparation of a compound of formula I as defined in claim 1 wherein Y is $C=O$, X is $CH=CH$ and $R^1$ and $R^2$ together represent a bond, by oxidizing a corresponding compound of formula I wherein X is $(CH_2)_2$,
(d) Preparation of a compound of formula I wherein Y is $C=O$, X is $(CH_2)_n$, $R^1$ is H and $R^2$ is H or $C_{1-6}$ alkyl, by reaction of a compound of formula II:

(II)

wherein R is H or $C_{1-3}$ alkyl, $R^{1a}$ is H, $R^{2a}$ is H or $C_{1-6}$ alkyl, and X is $(CH_2)_n$, or an acid addition salt thereof, with a hydrazine of formula III:

$Ar^1$ NHNH$_2$   (III)

wherein $Ar^1$ is as hereinbefore defined, or an acid addition salt thereof, and optionally after anyone of steps (a) to (d) forming a pharmaceutically acceptable deivative.

10. A method of treatment or prophylaxis of an allergic or an inflammatory disorder, which comprises administering a therapeutically effective amount of a compound of formula (1) as defined in claim 1, or a pharmaceutically acceptable derivative thereof, to a person suffering from or susceptible to said disorder.

* * * * *